US012754312B2

(12) United States Patent
Seong et al.

(10) Patent No.: US 12,754,312 B2
(45) Date of Patent: Oct. 6, 2026

(54) APPARATUS FOR CONTROLLING ULTRASONIC IRRADIATION, METHOD FOR CONTROLLING THEREOF

(71) Applicant: GODIUS CO., LTD., Seoul (KR)

(72) Inventors: Si Yong Seong, Seoul (KR); Hyun Sup Park, Seoul (KR); Tae Hyun Hwang, Seoul (KR); Dong Hwan Kang, Seoul (KR)

(73) Assignee: Godius Co., Ltd., Seoul (KR)

( * ) Notice: Subject to any disclaimer, the term of this patent is extended or adjusted under 35 U.S.C. 154(b) by 302 days.

(21) Appl. No.: 18/396,452

(22) Filed: Dec. 26, 2023

(65) Prior Publication Data

US 2025/0102668 A1 Mar. 27, 2025

(30) Foreign Application Priority Data

Sep. 26, 2023 (KR) ........................ 10-2023-0129402

(51) Int. Cl.
*G01S 15/89* (2006.01)
*A61B 8/00* (2006.01)
(Continued)

(52) U.S. Cl.
CPC ........ *G01S 15/8936* (2013.01); *A61B 8/0883* (2013.01); *A61B 8/4245* (2013.01);
(Continued)

(58) Field of Classification Search
CPC .......... A61N 7/02; A61B 90/36; A61B 90/50; A61B 8/0883; A61B 8/4245; G16H 20/40;
(Continued)

(56) References Cited

U.S. PATENT DOCUMENTS 3,986,160 A * 10/1976 Turner ................ G01S 15/8968 367/101
6,216,538 B1 * 4/2001 Yasuda .................. G10K 15/02 73/570.5
(Continued)

FOREIGN PATENT DOCUMENTS

CN 112888370 A 6/2021
JP 6861624 B2 4/2021
(Continued)

OTHER PUBLICATIONS

French Search Report and Written Opinion regarding Application No. FR2315087, Jan. 9, 2025.
(Continued)

*Primary Examiner* — Helen C Kwok
(74) *Attorney, Agent, or Firm* — Leydig, Voit & Mayer, Ltd.

(57) ABSTRACT

An apparatus for controlling an ultrasonic irradiation device according to an aspect of the present disclosure may include: a memory; a communication module configured to perform communication with the ultrasonic irradiation device; and a processor configured to control the ultrasonic irradiation device, the processor is configured to calculate a moving position based on: a first offset distance value between an ultrasonic probe and a marker stored in the memory, a second offset distance value between an ultrasonic irradiation module and a camera stored in the memory, and a first distance value, a second distance value, or a third distance value between a center position of the camera and a position of the marker in an image of an irradiation area obtained from the camera through the communication module.

20 Claims, 14 Drawing Sheets

(51) Int. Cl.
*A61B 8/08* (2006.01)
*A61B 90/00* (2016.01)
*A61B 90/50* (2016.01)
*A61N 7/02* (2006.01)
*G01S 7/52* (2006.01)
*G16H 20/40* (2018.01)
*G16H 50/20* (2018.01)

(52) U.S. Cl.
CPC .............. *A61B 90/36* (2016.02); *A61B 90/50* (2016.02); *A61N 7/02* (2013.01); *G01S 7/52085* (2013.01); *G01S 15/8993* (2013.01); *G16H 20/40* (2018.01); *G16H 50/20* (2018.01)

(58) Field of Classification Search
CPC . G16H 50/20; G01S 15/8936; G01S 15/8993; G01S 7/52085
See application file for complete search history.

(56) References Cited

U.S. PATENT DOCUMENTS

2003/0083536 A1 5/2003 Eshel et al.
2005/0154295 A1 7/2005 Quistgaard et al.
2011/0197679 A1* 8/2011 Kono .................... G01N 29/265 73/632
2015/0369651 A1* 12/2015 Nakajima ................ G01H 9/00 73/655
2016/0103221 A1* 4/2016 Oh ...................... G01S 7/52073 73/628
2016/0209502 A1* 7/2016 Kim .................... G01S 15/8913
2020/0015781 A1 1/2020 Hendriks et al.

FOREIGN PATENT DOCUMENTS

KR 20140095848 A 8/2014
KR 20160064574 A 6/2016
KR 20160145752 A 12/2016

OTHER PUBLICATIONS

Sachie Irisawa, et al., Robotic 3D Position Control of Therapeutic Ultrasonic Field by Ultrasound Image Information, The 2012 Biomedical Engineering International Conference (BMEiCon-2012), Dec. 2012, pp. 1-4, IEEE, Tokyo, Japan.
Chih Yu An, et al., An Ultrasound-Guided Robotic Hifu Ablation System With Respiration Induced Displacement and Time Delay Compensation, Journal of Medical and Biological Engineering, Feb. 19, 2019, pp. 796-805, vol. 39, Springer.
S. Adam Strickberger, et al., Extracardiac Ablation of the Canine Atrioventricular Junction by Use of High-Intensity Focused Ultrasound, American Heart Association, Jul. 13, 1999, pp. 203-209, American Heart Association, Dallas, Texas, United States of America.
Taiwanese Patent Office, Notice of Examination Opinion from the Intellectual Property Office of the Ministry of Economic Affairs regarding Patent Application No. 112150497, Jun. 21, 2014.
Korean Patent Office, Preliminary Examination Results Notification regarding Application No. 10-2023-0129402, Dec. 4, 2023.

* cited by examiner (a) First target distance (b) Second target distance (c) Third target distance

APPARATUS FOR CONTROLLING ULTRASONIC IRRADIATION, METHOD FOR CONTROLLING THEREOF

CROSS-REFERENCE TO RELATED APPLICATIONS

A claim for priority under 35 U.S.C. § 119 is made to Korean Patent Application No. 10-2023-0129402 filed on Sep. 26, 2023, in the Korean Intellectual Property Office, the entire contents of which are hereby incorporated by reference.

BACKGROUND

1. Technical Field

The present disclosure relates to an apparatus for controlling an ultrasonic irradiation device and a method for controlling the same, and more particularly, to an apparatus for controlling an ultrasonic irradiation device using high intensity focused ultrasound and a method for controlling the same.

2. Description of Related Art

The most representative use of ultrasound in the medical field is an ultrasound imaging device using the transmission and reflection properties of ultrasound. For example, a device visualizes the reflected time and degree of intensity of ultrasound by penetrating the ultrasound through the organs of a human body and acquires sectional images within the human body.

Furthermore, a device burns off specific subcutaneous tissues such as tumors in the skin by using heat generated by a high intensity focused ultrasound (HIFU) or causes degeneration and regeneration of skin tissues, resulting in skin beauty or skin molding effects such as wrinkle improvement.

However, the conventional ultrasonic irradiation device has degraded accuracy of ultrasound irradiation since it was not possible to accurately move to the irradiation position of ultrasound.

In addition, the conventional ultrasound irradiation device has limitations in shortening the preparation time for ultrasound irradiation by moving to the irradiation position of ultrasound, and in efficient irradiation of ultrasound.

Prior Art Literature (Patent Document 1) Japanese Patent Registration No. 6861624 (published on Apr. 1, 2021)

SUMMARY

To solve the technical problem, the embodiment of the present disclosure is provided to improve an accuracy of ultrasound irradiation by accurately moving to an irradiation position of ultrasound.

Furthermore, the embodiment of the present disclosure is provided to reduce an ultrasound irradiation preparation time.

Furthermore, the embodiment of the present disclosure is provided to irradiate ultrasound efficiently.

Technical problems of the inventive concept are not limited to the technical problems mentioned above, and other technical problems not mentioned will be clearly understood by those skilled in the art from the following description.

According to an embodiment, an apparatus for controlling an ultrasonic irradiation device according to an aspect of the present disclosure may include: a memory; a communication module configured to perform communication with the ultrasonic irradiation device; and a processor configured to control the ultrasonic irradiation device, the processor is configured to calculate a moving position based on: a first offset distance value between an ultrasonic probe and a marker stored in the memory, a second offset distance value between an ultrasonic irradiation module and a camera stored in the memory, and a first distance value, a second distance value, or a third distance value between a center position of the camera and a position of the marker in an image of an irradiation area obtained from the camera through the communication module.

Furthermore, the processor may match position information of the marker and center position information of the camera based on the first distance value, the second distance value, or the third distance value.

Furthermore, the processor may control and move a moving part of the ultrasonic irradiation device through the communication module or control a movement of a bed through the communication module to match the position information of the marker to the center position information of the camera.

Furthermore, the processor may further calculate a moving position of the ultrasonic irradiation module based on a sensing distance obtained from a sensing module of the ultrasonic irradiation device through the communication module such that a distance between the ultrasonic irradiation module and the ultrasonic probe or a distance between the ultrasonic irradiation module and a human body is maintained at a predetermined distance.

Furthermore, the processor may control and move a moving part of the ultrasonic irradiation device through the communication module or control a movement of a bed through the communication module based on the calculated moving position such that the ultrasonic irradiation module moves to the calculated moving position.

Furthermore, the processor may receive an input of the first offset distance value and the second offset distance value through a correction UI and store the first offset distance value and the second offset distance value in the memory, and control a movement of the bed along X-axis position movement and Y-axis position movement of the bed associated with the first offset distance value and the second offset distance value to match an irradiation position of the ultrasonic irradiation module to an imaging position of the ultrasonic probe.

Furthermore, the processor may further control an alarm module of the ultrasonic irradiation device to notify a situation of being able to irradiate ultrasound of the ultrasonic irradiation device based on the irradiation position of the ultrasonic irradiation module coinciding with the imaging position of the ultrasonic probe.

Furthermore, the processor may further control the ultrasonic irradiation module of the ultrasonic irradiation device to irradiate ultrasound of the ultrasonic irradiation device based on the irradiation position of the ultrasonic irradiation module coinciding with the imaging position of the ultrasonic probe.

Furthermore, the processor may receive an approach distance to a human body obtained from a sensing module of the ultrasonic irradiation device, and control the ultrasonic irradiation module to irradiate ultrasound differently with a predetermined intensity, which is associated with each of target distances, when the approach distance is a predetermined target distance.

Furthermore, the processor may receive a tumor position of an internal organ of a human body obtained from a sensing module of the ultrasonic irradiation device, and control the ultrasonic irradiation module to irradiate ultrasound differently with a predetermined strength, which is associated with each of target positions, when the tumor position is a predetermined target position.

Furthermore, the processor may further receive a tumor size of an internal organ of a human body obtained from a sensing module of the ultrasonic irradiation device, and control the ultrasonic irradiation module to irradiate ultrasound differently with a predetermined strength, which is associated with each of target sizes, when the tumor size is a predetermined target size.

Furthermore, a method for controlling an ultrasonic irradiation device performed by a control apparatus according to another aspect of the present disclosure may include receiving an input of a first offset distance value between an ultrasonic probe and a marker, and receiving an input of a second offset distance value between an ultrasonic irradiation module and a camera; receiving a first distance value, a second distance value, or a third distance value between a center position of a camera and a position of the marker in an image of an irradiation area obtained from the camera; and calculating a moving position based on the first offset distance value, the second offset distance value, the first distance value and the second distance value.

Furthermore, a method for controlling an ultrasonic irradiation device performed by a control apparatus according to still another aspect of the present disclosure may include receiving an input of a first offset distance value between an ultrasonic probe and a marker, and receiving an input of a second offset distance value between an ultrasonic irradiation module and a camera; receiving a first distance value, a second distance value, or a third distance value between a center position of a camera and a position of the marker in an image of an irradiation area obtained from the camera; matching position information of the marker to center position information of the camera based on the first distance value, the second distance value, or the third distance value; and calculating a moving position based on the first offset distance value and the second offset distance value.

DETAILED DESCRIPTION

Figure 1:
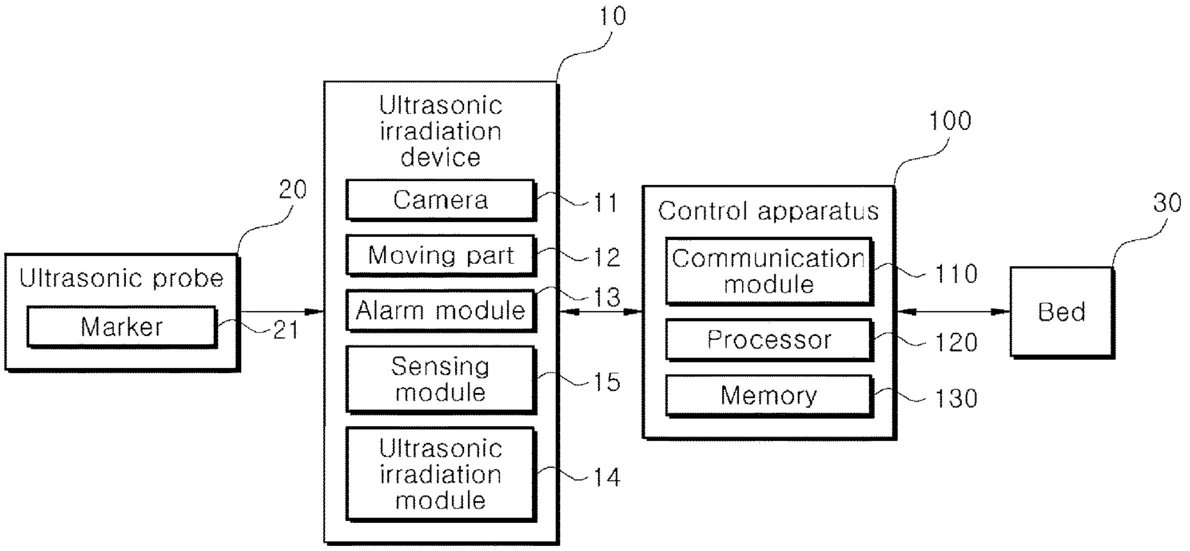
FIG. 1 is a diagram illustrating a configuration of an apparatus for controlling an ultrasonic irradiation device according to the present disclosure.

In the drawings, a same reference numeral designates a same element. The present disclosure does not describe all elements of embodiments, and general contents in the technical field to which the present disclosure belongs or repeated contents of the embodiments will be omitted. The terms, such as "unit, module, member, and block" may be embodied as hardware or software, and a plurality of "units, modules, members, and blocks" may be implemented as one element, or "a unit, a module, a member, or a block" may include a plurality of elements.

Throughout the present disclosure, when a part is referred to as being "connected" to another part, this includes direct connection and indirect connection, and the indirect connection may include connection via a wireless communication network.

Furthermore, when a certain part "includes" a certain element, other elements are not excluded unless explicitly described otherwise, and other elements may be included.

In the entire specification of the present disclosure, when any member is located "on" another member, this includes a case in which still another member is present between both members as well as a case in which one member is in contact with another member.

It will be understood that terms such as "first" and "second" may be used in the specification to distinguish an element from another element, and the elements are not restricted by the above terms.

A singular expression includes a plural expression unless there is a clear exception in the context.

An identification code in each of operational steps is used for the convenience of description and not for describing the order of the operational steps, and the operational steps may be implemented differently from the order described unless there is a specific order explicitly described in the context.

Hereinafter, the operational principle and the embodiments of the present disclosure will be described with reference to the accompanying drawings.

The high intensity focused ultrasound (HIFU) technology is a technology that burns a specific subcutaneous tissue, such as a tumor in the skin, using heat generated when high-intensity ultrasound is focused on a point in the skin. This is a similar principle to gathering sunlight with a magnifying glass and setting it on fire. Since ultrasound easily passes through body tissues, the HIFU irradiation method is performed in a completely non-invasive manner without a blade or even a needle. In other words, when the irradiation area of the skin is in close contact with the ultrasonic surface, a specific subcutaneous tissue such as a tumor is burned. In addition, the current HIFU irradiation method is used for uterine myoma, bone metastatic cancer, prostate cancer, breast cancer, pancreatic cancer, liver cancer, and kidney cancer.

Such an HIFU irradiation method may be implemented with an ultrasonic irradiation device.

In the specification of the present disclosure, the apparatus for controlling ultrasonic irradiation may include various types of devices capable of performing an operational process and providing a result to a user. For example, the apparatus for controlling ultrasonic irradiation according to the present disclosure may include all or either one of a computer, a server device, and a portable terminal.

Herein, the computer may include, for example, a notebook computer, a desktop computer, a laptop computer, a tablet PC, a slate PC, or the like equipped with a web browser.

The server device is a server of performing a communication with an external device and processing information, and may include an application server, a computing server, a database server, a file server, a mail server, a proxy server, a web server, or the like.

The portable terminal is a wireless communication device that secures portability and mobility and may include all types of handheld-based wireless communication device such as a terminal of Personal Communication System (PCS), Global System for Mobile communications (GSM), Personal Digital Cellular (PDC), Personal Handyphone System (PHS), Personal Digital Assistant (PDA), International Mobile Telecommunication (IMT)-2000, Code Division Multiple Access (CDMA)-2000, W-Code Division Multiple Access (W-CDMA), and Wireless Broadband Internet (WiBro), or a smartphone, and a wearable device such as a watch, a ring, a bracelet, an anklet, a necklace, glasses, a contact lens, or a head-mounted-device (HMD).

The apparatus for controlling ultrasonic irradiation according to the present disclosure may calculate a moving position based on a first offset distance value between an ultrasonic probe and a marker stored in a memory, a second offset distance value between an ultrasonic irradiation module of the ultrasonic irradiation device and a camera, and a first distance value, a second distance value, or a third distance value between a center position of the camera and a position of a marker in an image of an irradiation area obtained from the camera through a communication module.

The apparatus for controlling ultrasonic irradiation may improve the accuracy of ultrasonic irradiation by moving to an irradiation position of ultrasound accurately, reduce an ultrasonic irradiation preparation time, and irradiate ultrasound efficiently.

Hereinafter, the apparatus for controlling ultrasonic irradiation will be described in detail.

FIG. 1 is a diagram illustrating a configuration of an apparatus for controlling ultrasonic irradiation according to the present disclosure.

Referring to FIG. 1, a control apparatus 100 of an ultrasonic irradiation device 10 may include a communication module 110, a memory 130, and a processor 120.

The communication module 110 may perform communication with the ultrasonic irradiation device 10. In this case, the communication module 110 may include at least one of a wired communication module or a wireless communication module.

The wired communication module may include various cable communication modules such as Universal Serial Bus (USB), High Definition Multimedia Interface (HDMI), Digital Visual Interface (DVI), recommended standard 232 (RS-232), power line communication, and plain old telephone service (POTS) as well as various wired communication modules such as a Local Area Network (LAN) module, a Wide Area Network (WAN) module, and a Value Added Network (VAN) module.

The wireless communication module may include a wireless communication module that supports various wireless communication schemes such as Global System for Mobile Communication (GSM), Code Division Multiple Access (CDMA), Wideband Code Division Multiple Access (WCDMA), Universal Mobile Telecommunications System (UMTS), Time Division Multiple Access (TDMA), Long Term Evolution (LTE), 4G, 5G, 6G, and the like as well as a Wi-Fi module and a Wireless broadband module.

A controller may be implemented with the memory 130 storing algorithm for controlling operations of the elements in the apparatus and data for a program that reproduces the algorithm, and at least one processor 120 performing the operation described above by using the data stored in the memory 130. Here, the memory 130 and the processor 120 may be implemented in separated chips, respectively. Alternatively, the memory 130 and the processor 120 may be implemented in a single chip.

The memory 130 may store data that support various functions of the apparatus, programs for operating the controller, input/output data, a plurality of application programs (or applications) executed in the apparatus, and data and commands for operating the apparatus. At least a part of the application programs may be downloaded from an external server via a wireless communication.

The memory 130 may include at least a type of storage medium of flash memory type, hard disk type, Solid State Disk (SSD) type, Silicon Disk Drive (SDD) type, multimedia card micro type, memory of card type (e.g., SD or XD memory, and the like), random access memory (RAM), static random access memory (SRAM), read-only memory (ROM), electrically erasable programmable read-only memory (EEPROM), programmable read-only memory (PROM), magnetic memory, magnetic disk, and optical disk. Furthermore, the memory 130 may be separated from the apparatus but may be a database connected in wired or wireless manner.

The memory 130 may store data in relation to a control of the ultrasonic irradiation device 10. The processor 120 may perform an operation in relation to the control of the ultrasonic irradiation device 10.

The processor 120 may receive an input of a first offset distance value OD1 between an ultrasonic probe 20 and a marker 21 stored in the memory 130. In addition, the processor 120 may receive an input of a second offset distance value OD2 between an ultrasonic irradiation module 14 and a camera 11 stored in the memory 130. Further, the processor 120 may receive a first distance value, a second distance value, or a third distance value between a center position of the camera 11 and a position of the marker 21 in an image of an irradiation area obtained from the camera 11 through the communication module 110. In this case, the processor 120 may calculate a moving position based on the first offset distance value, the second offset distance value, the first distance value, the second distance value, or the third distance value.

In this case, the processor 120 may match position information of the marker 21 and center position information of the camera 11 by moving a bed 30 in X-axis and Y-axis directions based on the first distance value and the second distance value. Here, the processor 120 may control and move a moving part 12 of the ultrasonic irradiation device 10 through the communication module 110 or control a movement of the bed 30 through the communication module 110 to match the position information of the marker 21 to the center position information of the camera 11. In this case, the processor 120 may calculate a moving position based on the position in which the first offset distance value OD1, the second offset distance value OD2, the position information of the marker 21, and the center position information of the camera 11 are matched.

On the other hand, the processor 120 may match the position information of the marker 21 and the center position information of the camera 11 by moving the bed 30 in X-axis and Y-axis directions based on the third distance value. Here, the processor 120 may control and move the moving part 12 of the ultrasonic irradiation device 10 through the communication module 110 or control a movement of the bed 30 through the communication module 110 to match the position information of the marker 21 to the center position information of the camera 11. In this case, the processor 120 may calculate a moving position based on the position in which the first offset distance value OD1, the second offset distance value OD2, the position information of the marker 21, and the center position information of the camera 11 are matched.

The processor 120 may further calculate a moving position of the ultrasonic irradiation module 14 based on a sensing distance obtained from a sensing module 15 of the ultrasonic irradiation device 10 through the communication module 110 to maintain a distance between the ultrasonic irradiation module 14 and the ultrasonic probe 20 or a distance between the ultrasonic irradiation module 14 and a human body S.

The processor 120 may control and move the moving part 12 of the ultrasonic irradiation device 10 through the communication module 110 or control a movement of the bed 30 through the communication module 110 based on the calculated moving position such that the ultrasonic irradiation module 14 moves to the calculated moving position.

In this case, the processor 120 may receive an input of the first offset distance value and the second offset distance value through a correction UI and store the first offset distance value and the second offset distance value in the memory 130, and control a movement of the bed 30 along X-axis position movement and Y-axis position movement of the bed 30 associated with the first offset distance value and the second offset distance value to match an irradiation position of the ultrasonic irradiation module 14 to a imaging position of the ultrasonic probe 20.

The processor 120 may further control an alarm module 13 of the ultrasonic irradiation device 10 to notify a situation of capable of irradiating ultrasound of the ultrasonic irradiation device 10 based on the irradiation position of the ultrasonic irradiation module 14 being coincide with the imaging position of the ultrasonic probe 20. In this case, a user may move the ultrasonic irradiation module 14 of the ultrasonic irradiation device 10 in a Z-axis direction and irradiate ultrasound onto the irradiation area of the human body by using the ultrasonic irradiation module 14.

The processor 120 may further control the ultrasonic irradiation module 14 of the ultrasonic irradiation device 10 to irradiate ultrasound of the ultrasonic irradiation device 10 based on the irradiation position of the ultrasonic irradiation module 14 being coincide with the imaging position of the ultrasonic probe 20. In this case, the processor 120 may control the moving part 12 to move the ultrasonic irradiation module 14 in the z-axis direction, and may control the ultrasonic irradiation module 14 to irradiate ultrasound onto the irradiation area of the human body.

The communication module 110 may further receive an approach distance from the human body obtained from the sensing module 15 of the ultrasonic irradiation device 10. In this case, when the approach distance is a preset target distance, the processor 120 may further control the ultrasonic irradiation module 14 to irradiate ultrasound differently with a predetermined intensity, which is associated with each of target distances.

The communication module 110 may further receive a tumor position of an internal organ of the human body obtained from the sensing module 15 of the ultrasonic irradiation device 10. In this case, when the tumor position is a preset target position, the processor 120 may further control the ultrasonic irradiation module 14 to irradiate ultrasound differently with a predetermined intensity, which is associated with each of target positions. The communication module 110 may further receive a tumor size of an internal organ of the human body obtained from the sensing module 15 of the ultrasonic irradiation device 10. In this case, when the tumor size is a preset target size, the processor 120 may further control the ultrasonic irradiation module 14 to irradiate ultrasound differently with a predetermined intensity, which is associated with each of target sizes.

FIGS. 2 to 7 are flowcharts illustrating a control method of an ultrasonic irradiation device according to the present disclosure. FIGS. 8 to 14 are diagrams illustrating examples of processes for controlling an ultrasonic irradiation device through the control apparatus shown in FIG. 1.

Figure 2:
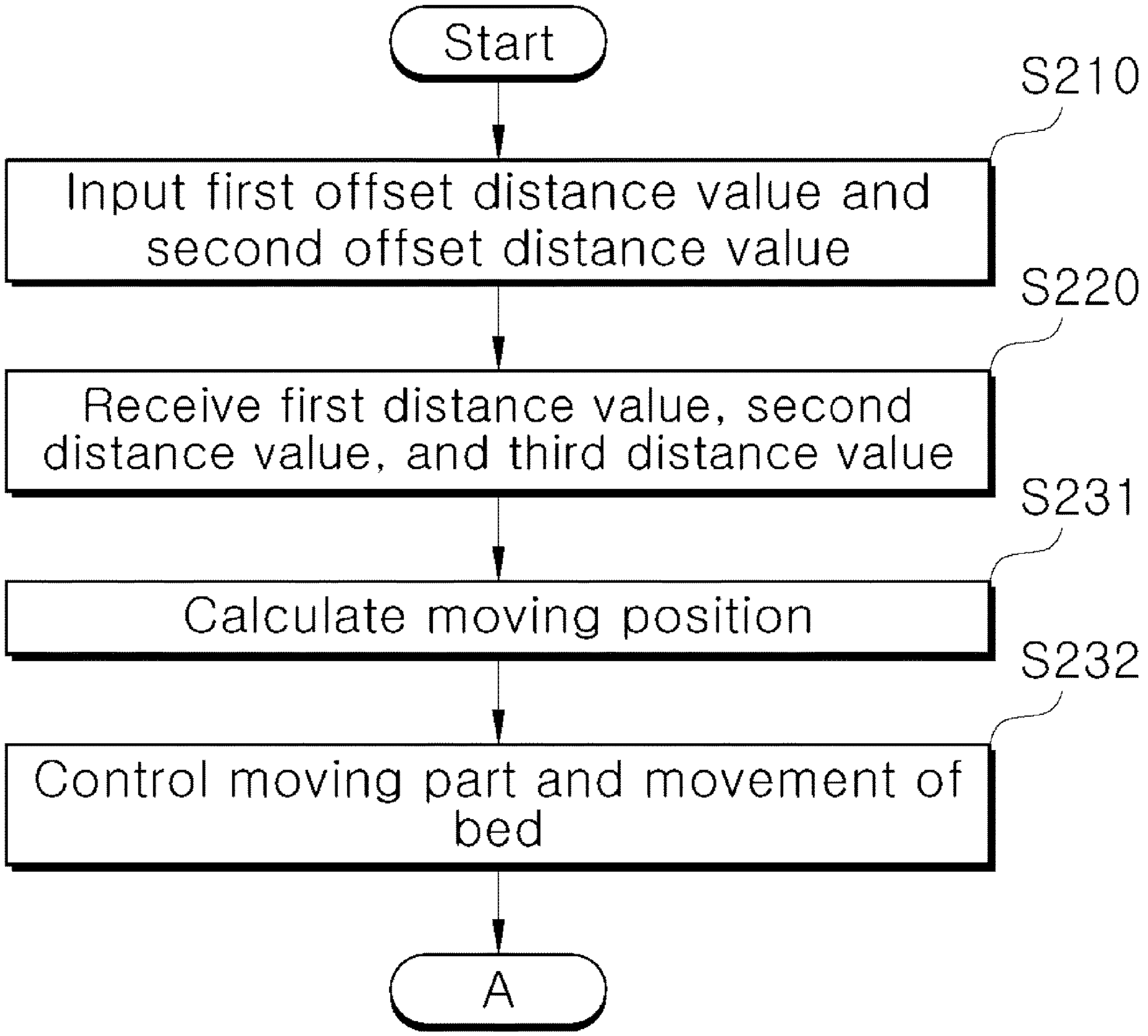
FIGS. 2 to 7 are flowcharts illustrating a control method of an ultrasonic irradiation device according to the present disclosure.
Figure 3:
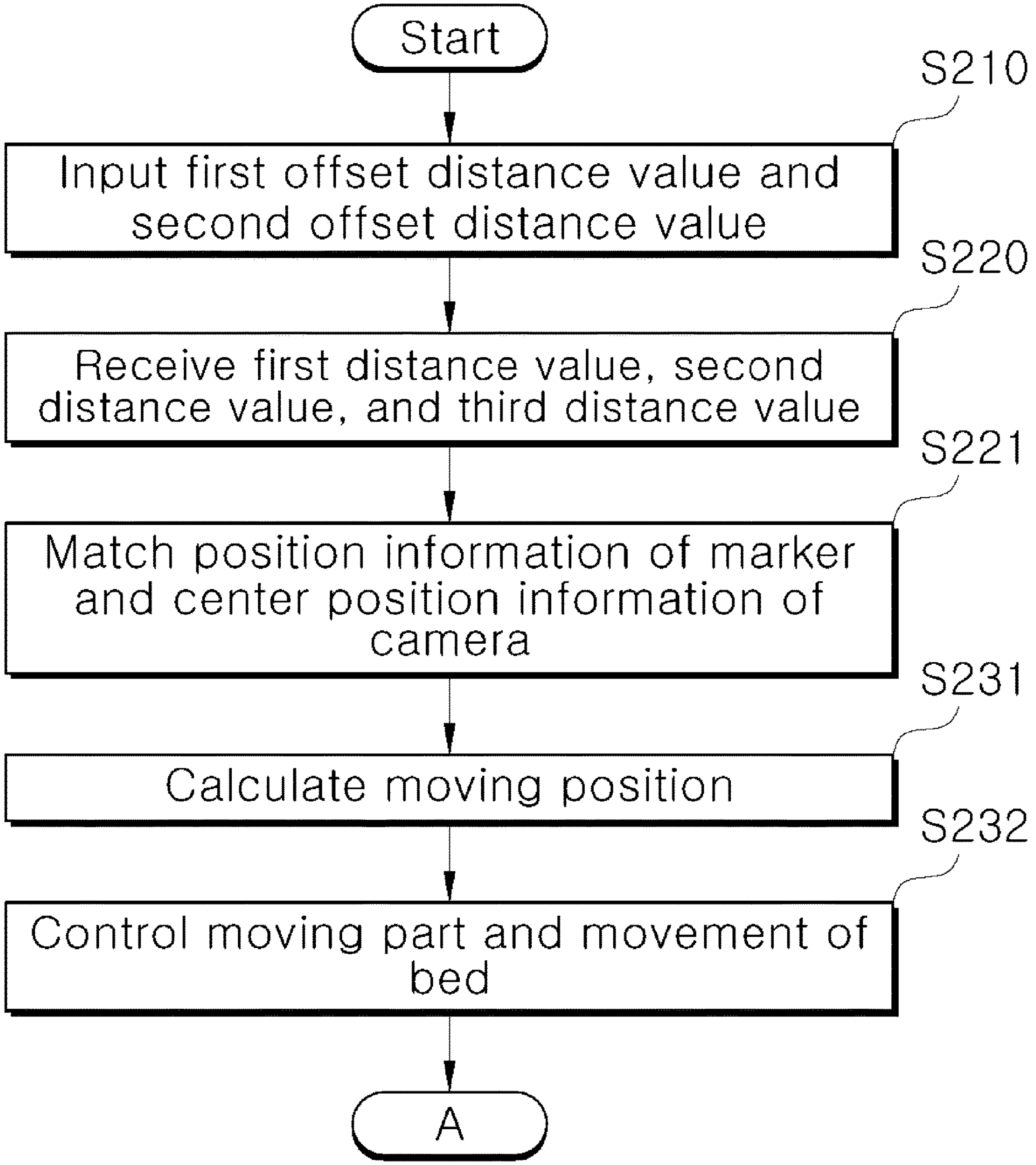

Referring to FIGS. 2 and 3, the control method may include an input operation S210, a reception operation S220, a matching operation S221, a calculation operation S231, and a control operation S232.

The input operation S210 may include receiving an input of the first offset distance value between the ultrasonic probe 20 and the marker 21 stored in the memory 130, and receiving an input of the second offset distance value between the ultrasonic irradiation module 14 and the camera 11 stored in the memory 130.

Figure 8:
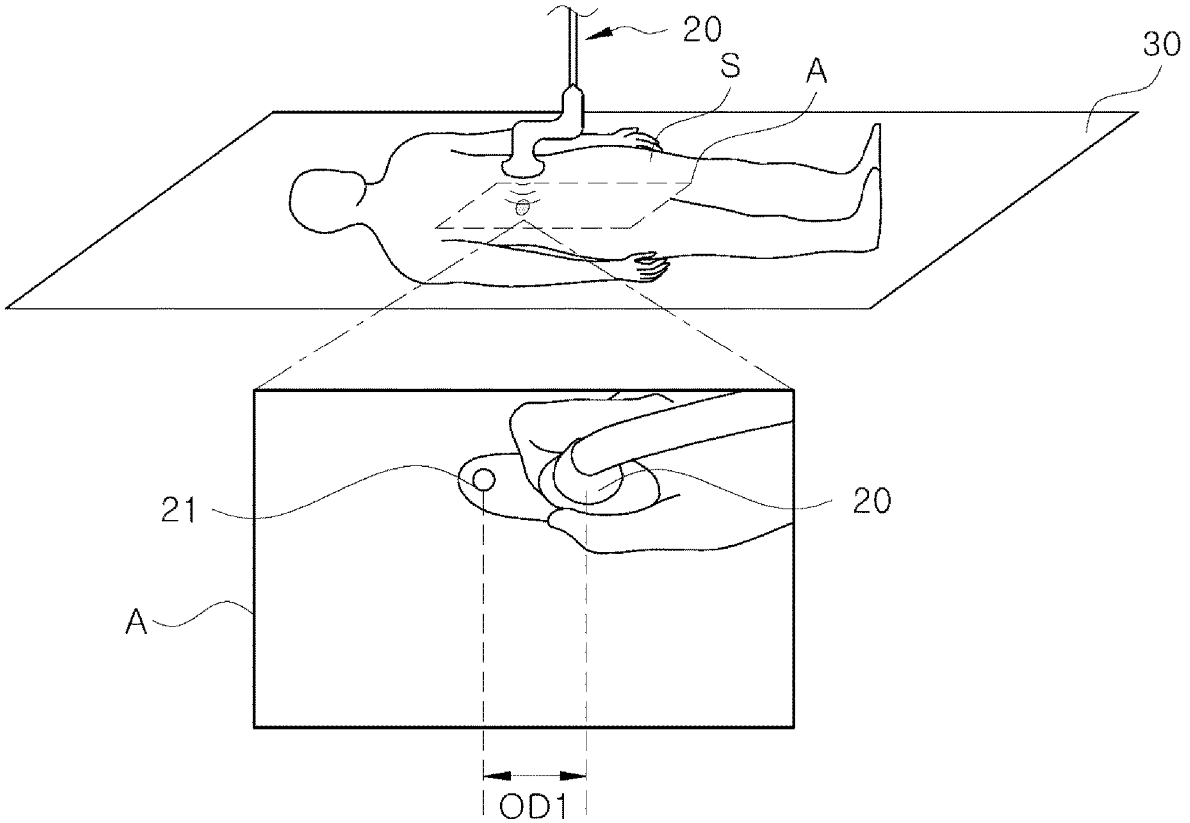
FIGS. 8 to 14 are diagrams illustrating examples of processes for controlling an ultrasonic irradiation device through the control apparatus shown in FIG. 1.

Here, as shown in FIG. 8, the first offset distance value OD1 may be a preset offset design value between the ultrasonic probe 20 and the marker 21. Here, the marker 21 may be formed to one side of the ultrasonic probe 20. In this case, the ultrasonic probe 20 may scan an irradiation area A through a transmission and reception of ultrasound. In other words, a user may scan the irradiation area A to identify the irradiation area A by using the ultrasonic probe 20.

Figure 9:
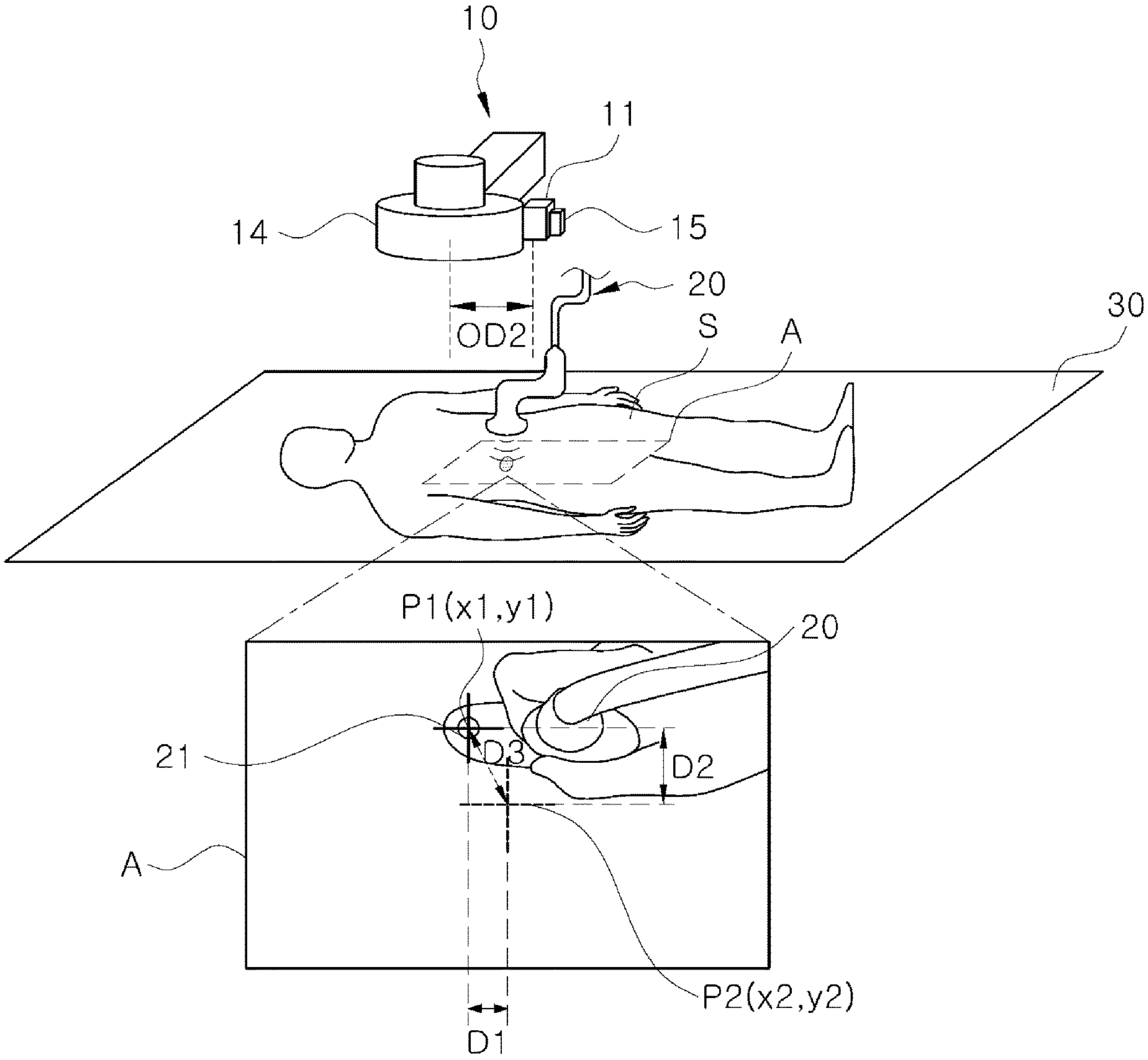

In addition, as shown in FIG. 9, the second offset distance value OD2 may be a preset offset design value between the ultrasonic irradiation module 14 and the camera 11. In this case, the camera 11 may be disposed at outside the ultrasonic irradiation module 14.

For example, the camera 11 may be provided as a video camera that uses an image sensing module. The video camera may be disposed in a stereo-type structure to obtain a left image and a right image to implement a three-dimensional stereoscopic image. In another example, the camera 11 may be provided as an AI camera. The AI camera may finely adjust the image recognized through a wide-angle sensing module created to imitate the human retina by using a brain neural network algorithm. The AI camera may adjust a shutter speed, a light exposure, a saturation, a color concentration, a dynamic range, a contrast, and the like. In addition, the AI camera may output the captured image as a high-quality image.

The reception operation S220 may include receiving the first distance value, the second distance value, or the third distance value between a center position of the camera 11 and a position of the marker 21 in an image of an irradiation area obtained from the camera 11 through the communication module 110.

In this case, as shown in FIG. 9, the processor 120 may receive position information P1 of the marker 21 in the image of the irradiation area A obtained from the camera 11 and center position information P2 of the camera 11. Here, the position information P1 of the marker 21 may be a first position coordinate value (x1, y1), and the center position information P2 of the camera 11 may be a second position coordinate value (x2, y2). In this case, the processor 120 may receive a first distance value D1, a second distance value D2, or a third distance value D3 based on the first position coordinate value (x1, y1) and the second position coordinate value (x2, y2).

In the calculation operation S231, a moving position may be calculated by the processor 120 based on the first offset distance value OD1, the second offset distance value OD2, the first distance value D1, and the second distance value D2, or the third distance value D3.

In addition, as shown in FIG. 3, in the matching operation S221, the position information P1 of the marker 21 and the center position information P2 of the camera 11 may be matched by the processor 120 by moving the bed 30 along the X and Y axes based on the first position coordinate value (x1, y1) and the second position coordinate value (x2, y2). Here, in order to match the position information P1 of the marker 21 and the center position information P2 of the camera 11, the processor 120 may control the moving part 12 of the ultrasonic irradiation device 10 through the communication module 110, or may control the movement of the bed 30 through the communication module 110. In this case, in the calculation operation S231, a moving position may be calculated by the processor 120 based on the position where the first offset distance value OD1, the second offset distance value OD2, the position information P1 of the marker 21 and the center position information P2 of the camera 11 coincide.

Here, the processor 120 may further calculate the moving position of the ultrasonic irradiation module 14 based on the sensing distance obtained from the sensing module 15 of the ultrasonic irradiation device 10 through the communication module 110 to maintain the distance between the ultrasonic irradiation module 14 and the ultrasonic probe 20 or the ultrasonic irradiation module 14 and the human body S at a predetermined distance. In this case, in the case that the sensing distance obtained from the sensing module 15 reaches a target distance for maintaining the preset predetermined distance, the processor 120 may calculate the moving position of the ultrasonic irradiation module 14 corresponding to the target distance. For example, the sensing module 15 may be a distance sensor.

In the control operation S232, the processor 120 may control the moving part 12 of the ultrasonic irradiation device 10 through the communication module 110 or control the movement of the bed 30 through the communication module 110 based on the calculated moving position so that the ultrasonic irradiation module 14 is moved to the calculated moving position.

Figure 10:
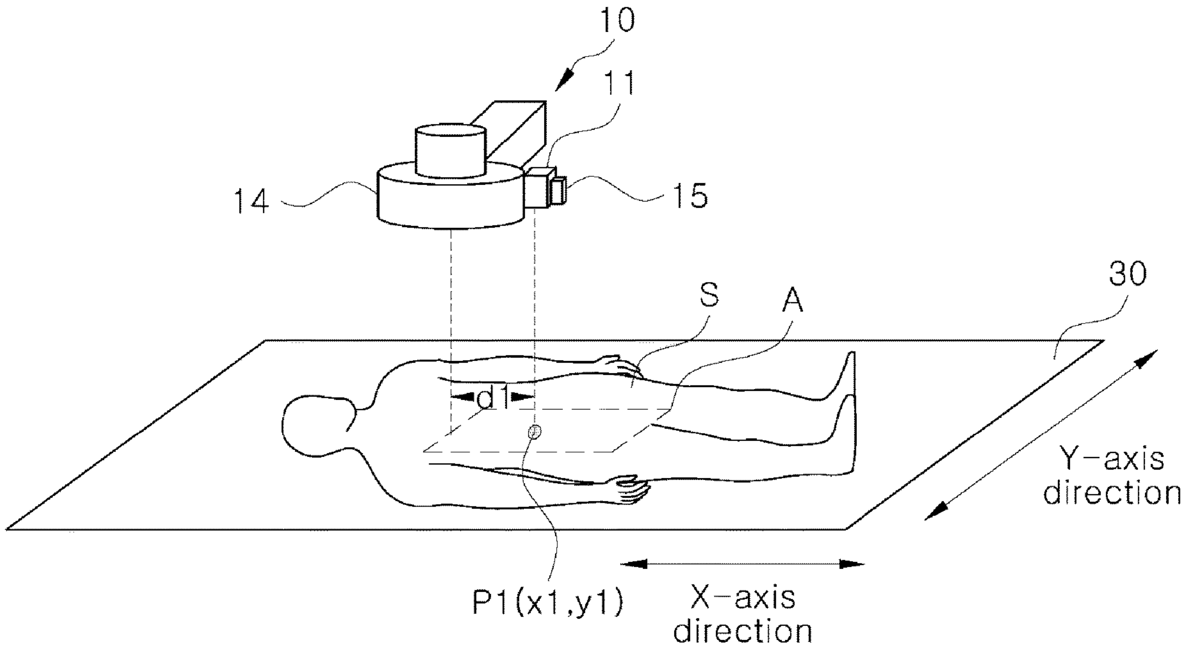

Here, as shown in FIG. 10, the processor 120 may receive the first offset distance value OD1 and the second offset distance value OD2 through the correction UI, store the first offset distance value OD1 and the second offset distance value OD2 in the memory 130, and control the movement of the bed 30 so that the irradiation position of the ultrasonic probe 14 and the imaging position of the ultrasonic probe 20 coincide with each other according to the X-axis position movement and the Y-axis position movement of the bed 30 associated with the first offset distance value OD1 and the second offset distance value OD2. In this case, a moving distance d1 may be controlled according to the X-axis position movement and the Y-axis position movement of the bed 30.

Here, even in the case that the irradiation position of the ultrasonic irradiation module 14 and the imaging position of the ultrasonic probe 20 match, the processor 120 may perform the correction since there is a distance difference between the marker 21 and the image of the irradiation area A. In addition, the processor 120 may also correct the distance between the ultrasonic irradiation module 14 and the camera 11.

In this case, the user may input a correction value by using the correction UI based on a GUI program, and the processor 120 may control the movement of the bed 30 to move the X-axis position and Y-axis position of the bed 30 where a patient is lying based on the input correction value and the position information P1 of the marker 21.

According to the processor 120, the irradiation position of the ultrasonic irradiation module and the imaging position of the ultrasonic probe 20 coincide exactly, so that the accuracy of ultrasonic irradiation may be improved.

Meanwhile, the processor 120 may automatically position the ultrasonic probe 20 at a pre-scanned position through the camera 11 to promote the user convenience.

For example, a configuration UI based on the GUI program may include a first UI for displaying an image acquired by the camera 11, a second UI for setting an image capturing position of the camera 11, a third UI for setting an offset design value between the camera 11 and the ultrasonic irradiation module 14, a fourth UI for setting an offset design value between the ultrasonic probe 20 and the marker 21, and a fifth UI for inputting a communication setting value with the ultrasonic sensor for measuring a body thickness of a patient.

Here, through the second UI, the user may move to a position where the user may capture an image while watching the image of the camera 11, and then store the corresponding position by pressing a setting button. Through the third UI, the user may manually input an offset design value between the camera 11 and the ultrasonic irradiation module 14. In this case, the third UI may display the design value as Default. Through the fourth UI, the user may manually input an offset design value between the ultrasonic probe 20 and the marker 21. In this case, the fourth UI may display the design value as Default. Through the fifth UI, the user may identify whether the measurement is normal by inputting a communication setting value with the ultrasonic sensor for measuring the body thickness of a patient and then pressing a measurement button. Thereafter, the user may place the patient in the irradiation area A of the camera 11 using the correction UI based on the GUI program, and then check for myoma or cancer present in internal organs of the human body S such as the uterus, ovary, heart, kidney, breast, and the like through the ultrasonic probe 20, and select the final position.

Thereafter, the user may finally check the myoma or cancer using the correction UI based on the GUI program, and then, move the ultrasonic irradiation module 14 to the imaging position of the camera 11 by pressing an alignment move button on a manipulation panel of the control apparatus 100. In this case, the user may move the camera 11 along the X-axis, Y-axis, and Z-axis directions corresponding to the preset imaging position of the camera 11 using the manipulation panel. In addition, the user may measure the body thickness of a patient using the manipulation panel and correct and move the Z-axis of camera 11 so that the image of camera 11 is focused.

Later, the user may check a coordinate detection of the marker 21 obtained through the camera 11 and the corresponding result using the correction UI based on the GUI program. Here, the user may check whether the position of the marker 21 is detected. In this case, the distance conversion of the marker 21 may be automatically calculated as a millimeter conversion value per pixel unit of the image.

Thereafter, the user may find a position of the marker 21 using the correction UI based on the GUI program, remove the ultrasonic probe 20 from the patient's abdomen, and press the alignment move button on the manipulation panel to locate the ultrasonic probe 20 in the transducer to myoma or cancer. In this case, the processor 120 may add the first offset distance value OD1 between the ultrasonic probe 20 and the marker 21 and the second offset distance value OD2 between the camera 11 and the ultrasonic irradiation module 14, or subtract the first offset distance value OD1 between the ultrasonic probe 20 and the marker 21 and the second offset distance value OD2 between the camera 11 and the ultrasonic irradiation module, and control the X-axis position movement and the Y-axis position movement of the bed 30 so that the irradiation position of the ultrasonic probe 20 and the imaging position of the ultrasonic probe 20 face each other by adding or subtracting the first offset distance value OD1 and the second offset distance value OD2. Thereafter, after the movement of the bed 30 is completed, the user may move the ultrasonic irradiation module 14 along the Z-axis direction using the manipulation panel to bring it into close contact with the patient's abdomen, and then check whether the position of the myoma or cancer to be irradiated with ultrasound is correct.

Figure 4:
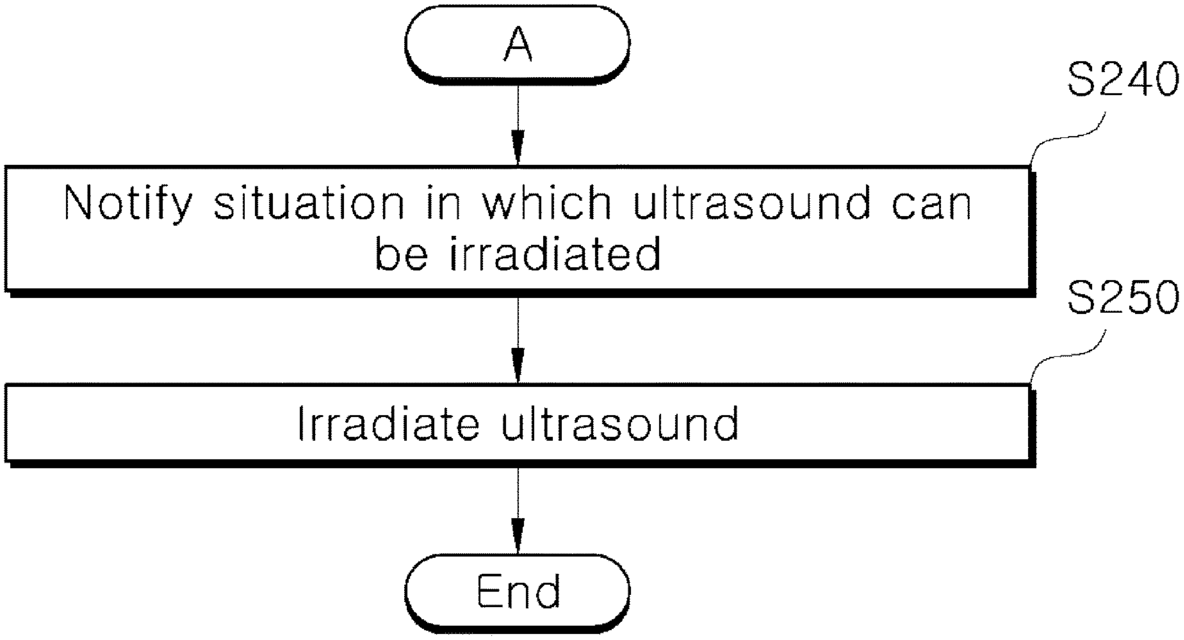

Referring to FIG. 4, the control method may further include an alarming operation S240.

In the alarming operation S240, in the case that the irradiation position of the ultrasonic irradiation module 14 and the imaging position of the ultrasonic probe 20 coincide, the processor 120 may control the alarm module 13 of the ultrasonic irradiation device 10 to notify a situation in which ultrasound of the ultrasonic irradiation device 10 can be irradiated. For example, the alarm module 13 may be provided with at least one of a display module or an LED for a visual notification, or a speaker for an audible notification. Here, as shown in FIG. 10, the user may move the ultrasonic irradiation module 14 of the ultrasonic irradiation device 10 along the Z-axis direction, and irradiate ultrasound onto the irradiation area A of the human body S using the ultrasonic irradiation module 14.

Referring to FIG. 4 to FIG. 7, the control method may further include an ultrasound irradiation operation S250.

In the ultrasound irradiation operation S250, in the case that the irradiation position of the ultrasonic irradiation module 14 and the imaging position of the ultrasonic probe 20 coincide, the processor 120 may further control the ultrasonic irradiation module 14 of the ultrasonic irradiation device 10 to irradiate ultrasound of the ultrasonic irradiation device 10. Here, as shown in FIG. 10, the processor 120 may control the moving part 12 to move the ultrasonic irradiation module 14 along the Z-axis direction, and the processor 120 may control the ultrasonic irradiation module 14 to irradiate ultrasound onto the irradiation area A of the human body S.

Figure 5:
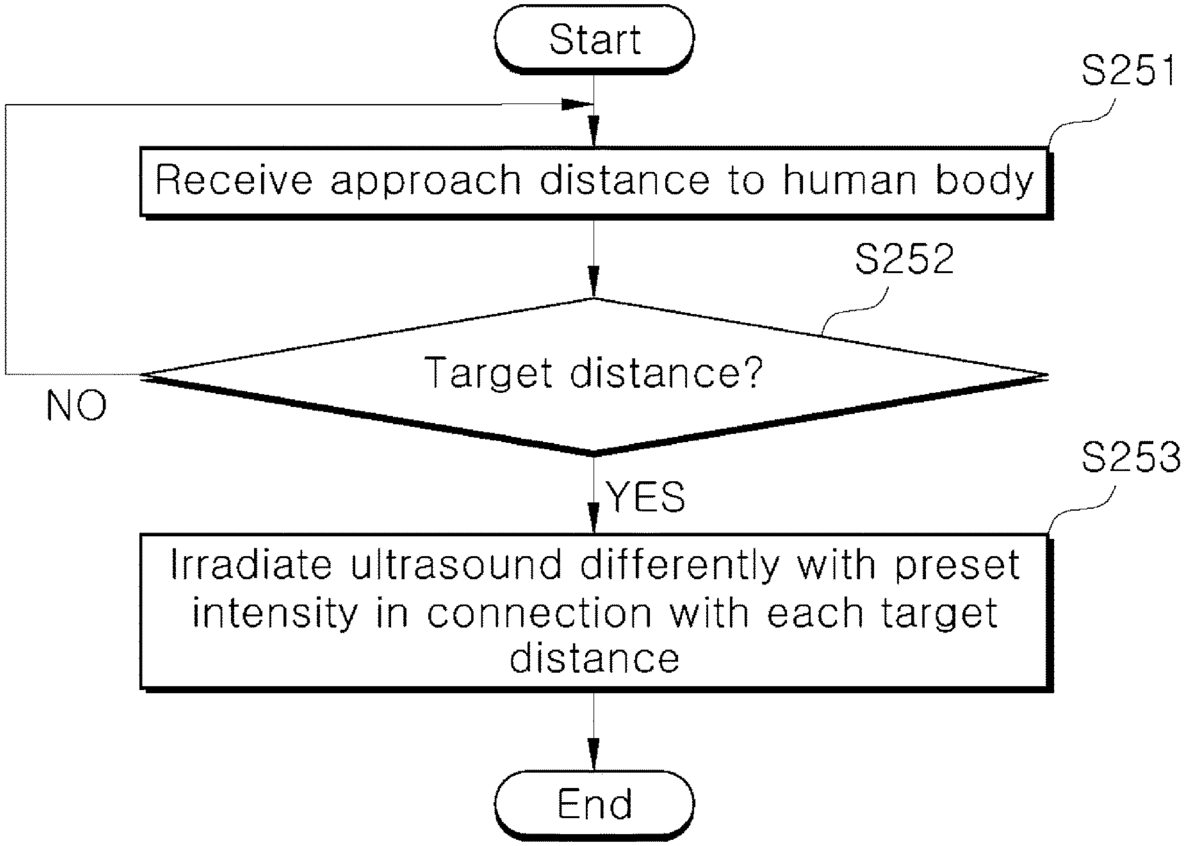

Referring to FIG. 5, the ultrasound irradiation operation S250 may further include a first reception operation S251, a first determination operation 252, and a first control operation S253.

In the first reception operation S251, an approach distance d2 to the human body S obtained from the sensing part 15 of the ultrasonic irradiation device 10 may be received through the communication module 110. Here, the sensing moduel 15 may be a distance sensor, and the communication module 110 may receive the approach distance d2 to the human body S obtained by the distance sensor. In other words, the sensing module 15 may sense a predetermined distance from the boundary surface of the human body S to the ultrasonic irradiation module 14. For example, the predetermined distance may be 200 mm to 250 mm, preferably 230 mm. In this case, the sensing module 15 may be provided outside the camera 11.

In the first determination operation 252, the processor 120 may determine whether the approach distance d2 is a preset target distance. In the first control operation 253, in the case that the approach distance d2 is the preset target distance, the processor 120 may control the ultrasonic irradiation module 14 to irradiate ultrasound differently with a preset intensity in connection with each target distance.

Figure 11:
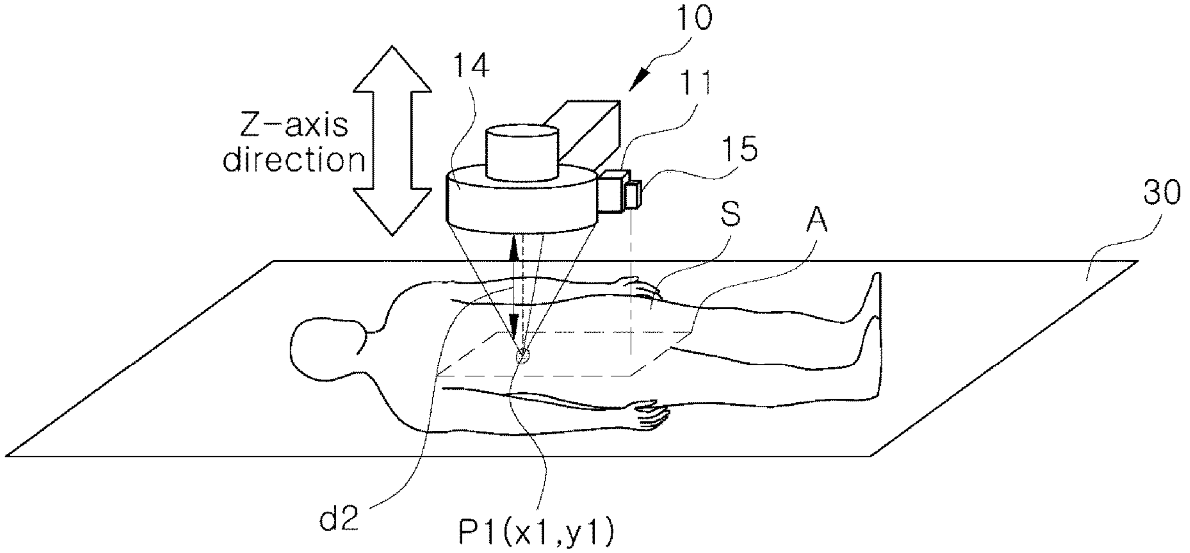
Figure 12:
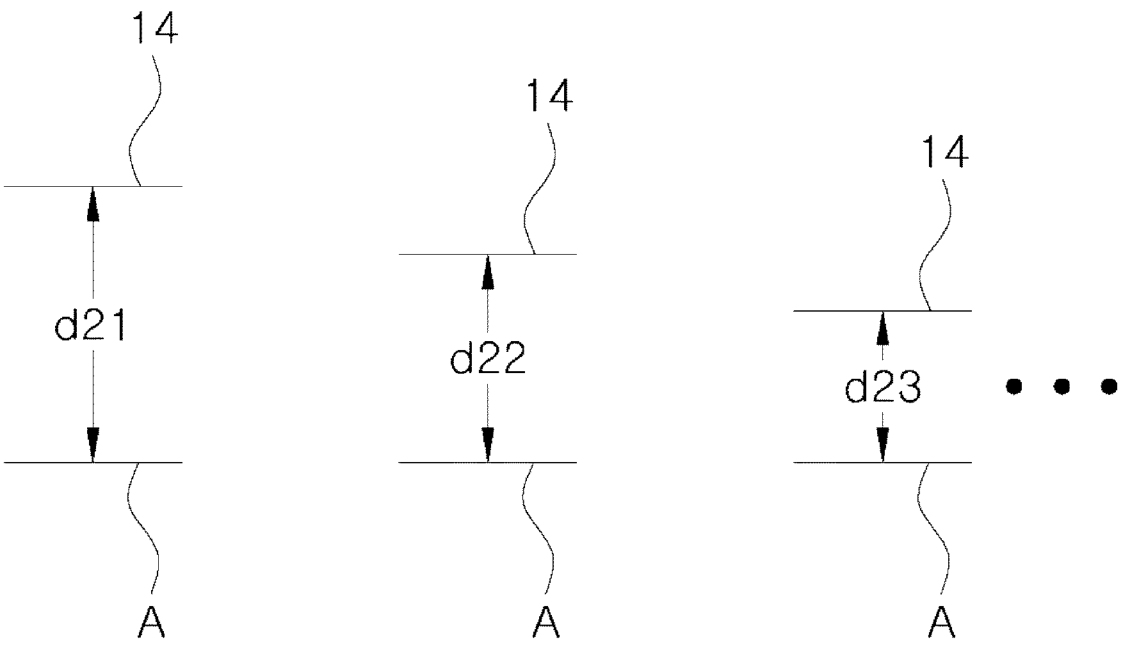

For example, as shown in FIG. 11 and FIG. 12, in the case that the approach distance d2 is a preset first target distance d21, the processor 120 may control the ultrasonic irradiation module 14 to irradiate the irradiation area A of the human body S with a preset strong level of intensity in connection with the first target distance d21. For another example, in the case that the approach distance d2 is a preset second target distance d22, the processor 120 may control the ultrasonic irradiation module to irradiate the irradiation area A of the human body S with a preset intermediate level of intensity in connection with the second target distance d22. For still another example, in the case that the approach distance d2 is a preset third target distance d23, the processor 120 may control the ultrasonic irradiation module 14 to irradiate the irradiation area A of the human body S with a preset weak level of intensity in connection with the third target distance d23.

Meanwhile, for the convenience of description, the present disclosure is illustrated and described the irradiation onto the irradiation area A of the human body S with three levels of intensity, the processor 120 may control the ultrasonic irradiation module 14 to irradiate the irradiation area A of the human body S with two levels or four or more levels of intensity.

Figure 6:
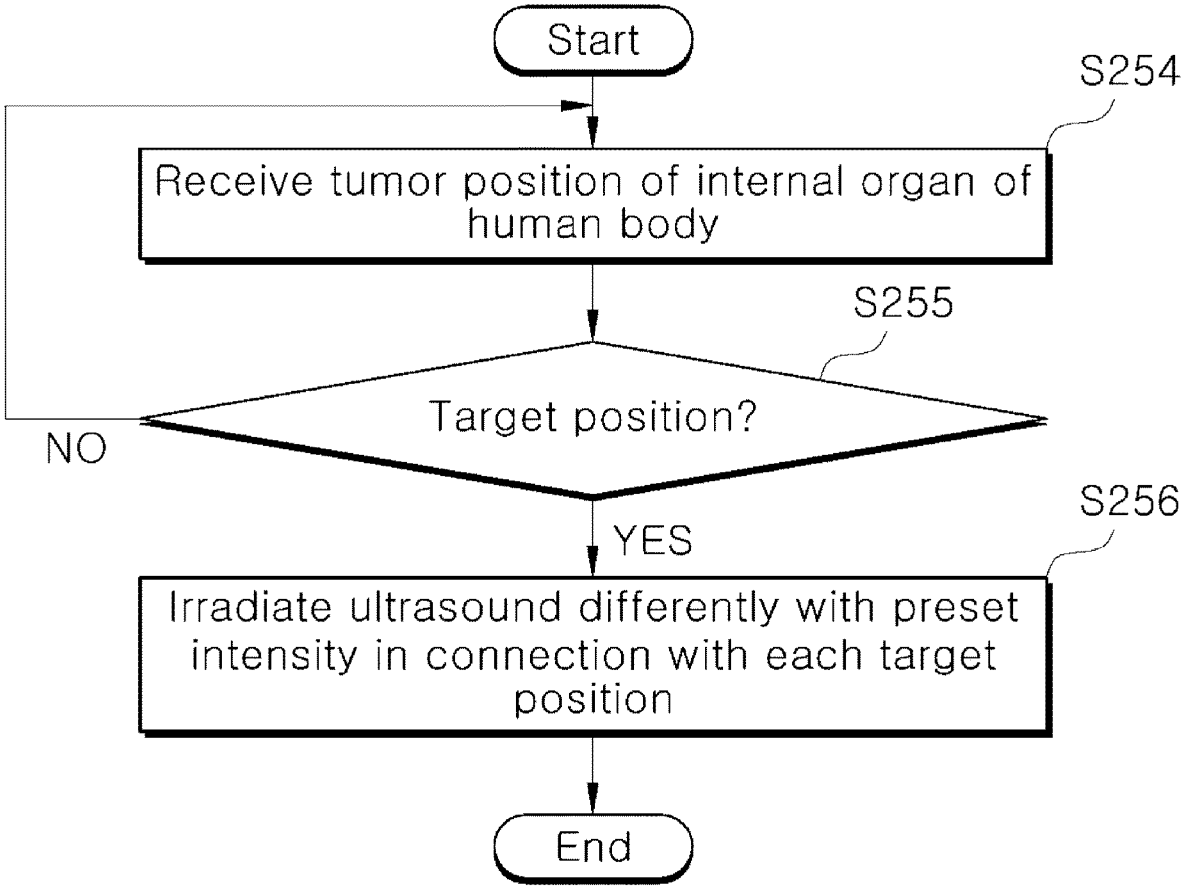

Referring to FIG. 6, the ultrasound irradiation operation S250 may further include a second reception operation S254, a second determination operation 255, and a second control operation S256.

In the second reception operation S254, a tumor position of the internal organ of the human body obtained from the sensing module 15 of the ultrasound irradiation device 10 may be received through the communication module 110. Here, the sensing module 15 may be a gamma camera or the ultrasonic probe. In this case, the gamma camera or the ultrasonic probe may accurately measure the myoma or cancer present in the human organs such as the uterus, ovaries, heart, kidney, breast, and the like in the human body. Here, the communication module 110 may receive the tumor position acquired by the gamma camera or ultrasonic probe. In this case, the sensing module 15 may be provided outside the camera 11.

In the second determination operation S255, the processor 120 may determine whether the tumor position is a preset target position. In the second control operation S256, in the case that the tumor position is the preset target position, the processor 120 may control the ultrasonic irradiation module 14 to irradiate ultrasound with a different preset intensity in connection with each target position.

Figure 13:
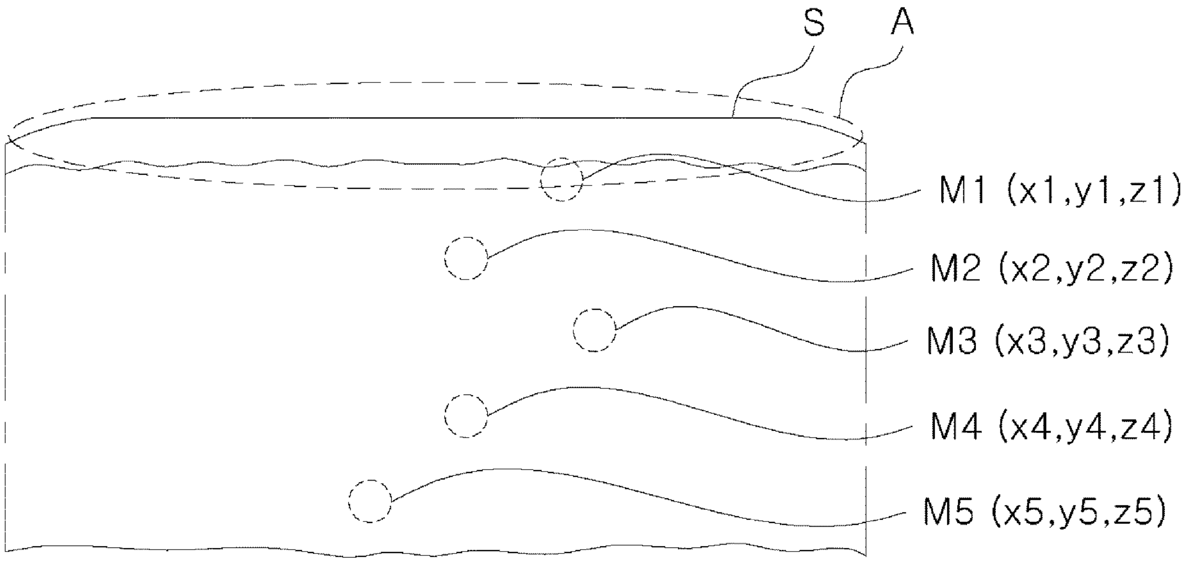

For example, as shown in FIG. 13, in the case that the tumor position is a preset first target position M1, the processor 120 may control the ultrasound irradiation module to irradiate the tumor of the breast with ultrasound at a customized intensity corresponding to the preset tumor position of the breast in connection with the first target position M1.

For another example, in the case that the tumor position is a preset second target position M2, the processor 120 may control the ultrasound irradiation module 14 to irradiate the tumor of the heart with ultrasound at a customized intensity corresponding to the preset tumor position of the heart in connection with the second target position M2.

For still another example, in the case that the tumor position is a preset third target position M3, the processor 120 may control the ultrasound irradiation module 14 to irradiate the tumor of the kidney with ultrasound at a customized intensity corresponding to the preset tumor position of the kidney in connection with the third target position M3.

For still another example, in the case that the tumor position is a fourth target position M4, the processor 120 may control the ultrasound irradiation module 14 to irradiate the tumor of the uterus with ultrasound at a customized intensity corresponding to the preset tumor position of the uterus in connection with the fourth target position M4.

For still another example, in the case that the tumor position is a preset fifth target position M5, the processor 120 may control the ultrasound irradiation module 14 to irradiate the tumor of the ovary with ultrasound at a customized intensity corresponding to the preset tumor position of the ovary in connection with the fifth target position M5.

On the other hand, for the convenience of description, the present disclosure has been illustrated and described to irradiate the tumors of five internal organs of the human body with ultrasound at customized intensities corresponding to the tumor positions of the five internal organs of the human body, but the processor 120 may control the ultrasound irradiation module 14 to irradiate the tumors of the internal organs with ultrasound at customized intensities corresponding to the tumor positions of six or more further subdivided internal organs of the human body. In this case, the customized intensity may be the same intensity for each tumor position of each internal organ of the human body, or may be different intensities.

Figure 7:
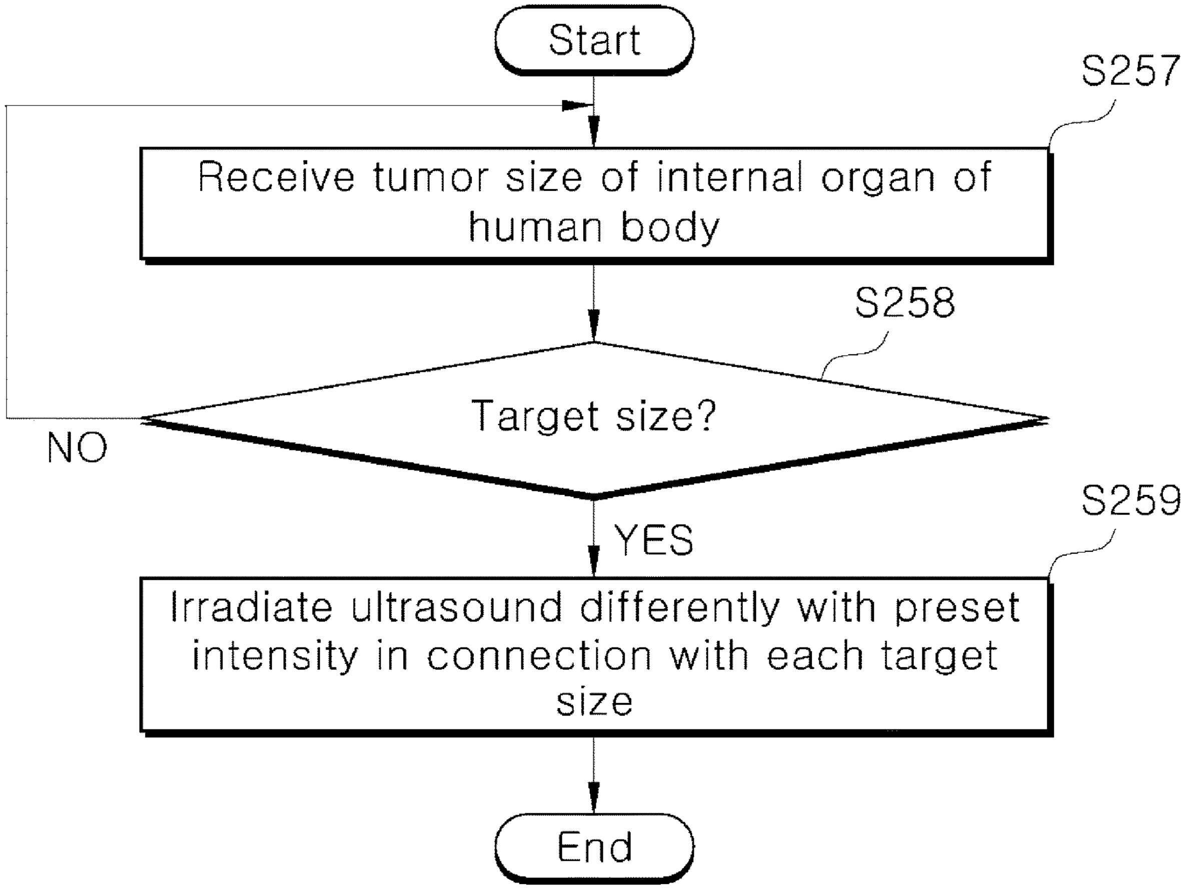

Referring to FIG. 7, the ultrasonic irradiation operation S250 may further include a third reception operation S257, a third determination operation S258, and a third control operation S259.

In the third reception operation S257, a tumor size of the internal organ of the human body obtained from the sensing module 15 of the ultrasound irradiation device 10 may be received through the communication module 110. Here, the sensing module 15 may be the gamma camera or the ultrasonic probe. In this case, the gamma camera or the ultrasonic probe may accurately measure the myoma or cancer present in the human organs such as the uterus, ovaries, heart, kidney, breast, and the like in the human body. Here, the communication module 110 may receive the tumor size acquired by the gamma camera or ultrasonic probe. In this case, the sensing module 15 may be provided outside the camera 11.

In the third determination operation S258, the processor 120 may determine whether the tumor size is a preset target size. In the third control operation S259, in the case that the tumor size is the preset target size, the processor 120 may control the ultrasonic irradiation module 14 to irradiate ultrasound at a different preset intensity in connection with each target size.

Figure 14:
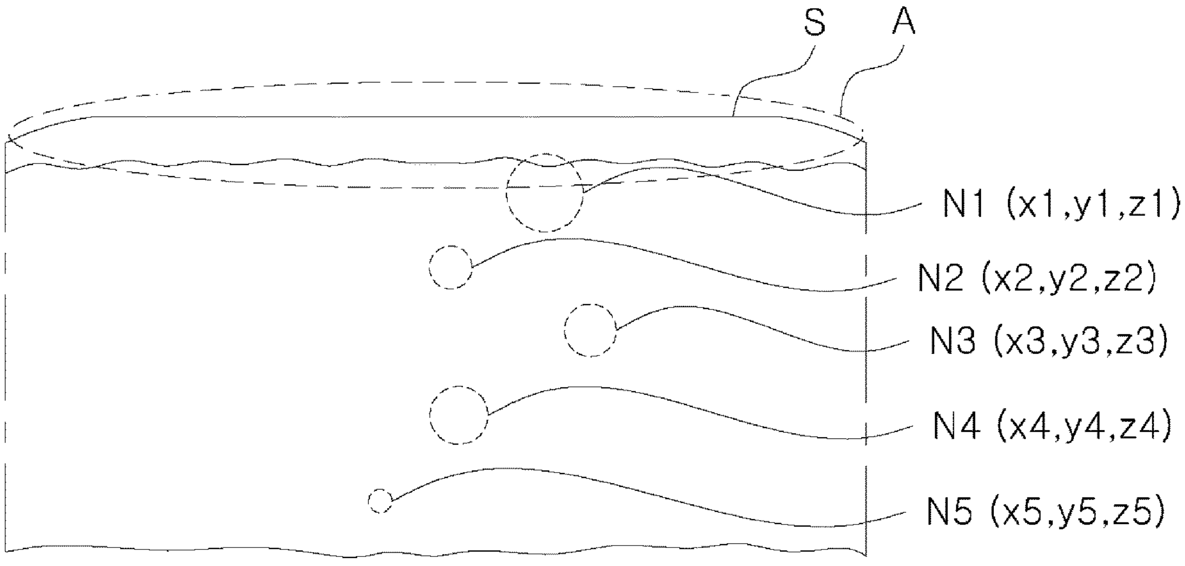

For example, as shown in FIG. 14, in the case that the tumor size is a preset first target size N1, the processor 120 may control the ultrasound irradiation module 14 to irradiate the tumor of the breast with ultrasound at a customized intensity corresponding to the preset tumor size of the breast in connection with the first target size N1.

For another example, in the case that the tumor size is a preset second target size N2, the processor 120 may control the ultrasound irradiation module 14 to irradiate the tumor of the heart with ultrasound at a customized intensity corresponding to the preset tumor size of the heart in connection with the second target size N2.

For still another example, in the case that the tumor size is a preset third target size N3, the processor 120 may control the ultrasound irradiation module 14 to irradiate the tumor of the kidney with ultrasound at a customized intensity corresponding to the preset tumor size of the kidney in connection with the third target size N3.

For still another example, in the case that the tumor size is a fourth target size N4, the processor 120 may control the ultrasound irradiation module 14 to irradiate the tumor of the uterus with ultrasound at a customized intensity corresponding to the preset tumor size of the uterus in connection with the fourth target size N4.

For still another example, in the case that the tumor size is a preset fifth target size N5, the processor 120 may control the ultrasound irradiation module 14 to irradiate the tumor of the ovary with ultrasound at a customized intensity corresponding to the preset tumor size of the ovary in connection with the fifth target size N5.

On the other hand, for the convenience of description, the present disclosure has been illustrated and described to irradiate the tumors of five internal organs of the human body with ultrasound at customized intensities corresponding to the tumor sizes of the five internal organs of the human body, but the processor 120 may control the ultrasound irradiation module 14 to irradiate tumors of the internal organs with ultrasound at customized intensities corresponding to the tumor sizes of six or more further subdivided internal organs of the human body. In this case, the customized intensity may be the same intensity for each tumor size of each internal organ of the human body, or may be different intensities.

The present disclosure may control the ultrasonic irradiation device 10 so that ultrasound is irradiated differently by at least one of an ultrasonic focusing depth, an ultrasonic irradiation position, an ultrasonic intensity, or an ultrasonic irradiation time preset for each depth of the human organ depending on the irradiation conditions.

Here, the ultrasonic focusing depth may be at least one of a deep depth, a medium depth, or a shallow depth preset for each depth of the human organ depending on the irradiation conditions. In addition, the ultrasonic irradiation position may be a full position or a partial position preset for each depth of the human organ depending on the irradiation conditions. In addition, the ultrasonic intensity may be at least one of a strong intensity, an intermediate intensity, or a weak intensity preset for each depth of the human organ depending on the irradiation conditions. In addition, the ultrasound irradiation time may be at least one of a quick irradiation time, an average irradiation time, or a late irradiation time preset for each depth of the human organ depending on the irradiation conditions. In this case, the present disclosure may increase the irradiation effect by controlling the ultrasonic irradiation time at rapid intervals and increasing the temperature again before the temperature decreases.

On the other hand, since the depth of human organ may vary from person to person within an area, at least one of the ultrasonic focusing depth, ultrasonic irradiation location, ultrasonic intensity, or ultrasonic irradiation time may be set to be finely adjusted within the area.

In addition, the present disclosure may control at least one of an angle or an irradiation direction of the ultrasonic irradiation device 10 so that the ultrasound is accurately irradiated to the human organ in the area with at least one of the depth or the intensity corresponding to the irradiation conditions based on at least one of angle information or irradiation direction information.

At least one element may be added or deleted in response to the performance of the elements shown in FIG. 1, FIG. 8 to FIG. 14. In addition, it will be easily understood by those skilled in the art that the relative positions of elements may be changed in response to the performance or structure of the system.

FIG. 2 to FIG. 7 illustrate that multiple operations are performed sequentially, but this is merely exemplary description of the technical concept of this embodiment, and those skill in the art to which this embodiment belongs may change the order described in FIG. 2 to FIG. 7 or may be variously modified to execute one or more of multiple operations in parallel within the scope not departing from the essential characteristics of this embodiment.

While the inventive concept has been described with reference to embodiments, it will be apparent to those skilled in the art that various changes and modifications may be made without departing from the spirit and scope of the inventive concept. Therefore, it should be understood that the above embodiments are not limiting, but illustrative.

Advantageous Effects

According to the technical solution to solve the problem according to the present disclosure, there is an effect of improving the accuracy of ultrasound irradiation by moving to an ultrasound irradiation position accurately.

In addition, according to the technical solution to solve the problem according to the present disclosure, there is an effect of reducing an ultrasound irradiation preparation time.

In addition, according to the technical solution to solve the problem according to the present disclosure, there is an effect of irradiating ultrasound efficiently.

The advantages of the present disclosure are not limited to the above-mentioned advantages, and other advantages, which are not specifically mentioned herein, will be clearly understood by those skilled in the art from the following description.

What is claimed is:

1. An apparatus for positioning an ultrasonic irradiation device, comprising:
a memory;
a communication interface for communication with the ultrasonic irradiation device; and
a processor configured to:
determine a moving position based on a first offset value stored in the memory, a second offset value stored in the memory, and a distance value, wherein the first offset value corresponds to a distance between an ultrasonic probe and a marker, wherein the second offset value corresponds to a distance between the ultrasonic irradiation device and a camera, and wherein the distance value corresponds to a distance between a center position of the camera and a position of the marker in an image obtained from the camera; and
control the ultrasonic irradiation device and/or a bed to move based on the determined moving position to match the position of the marker with the center position of the camera; and
wherein the processor is further configured to maintain a predetermined distance between the ultrasonic irradiation device and the ultrasonic probe or a predetermined distance between the ultrasonic irradiation device and a body based on a sensing distance obtained from a distance sensor of the ultrasonic irradiation device.

2. The apparatus of claim 1, wherein the processor is further configured to:
receive an input of the first offset value and the second offset value through a correction user interface (UI);
store the first offset value and the second offset value in the memory; and
control a movement of the bed along an X-axis and a Y-axis to match an irradiation position of the ultrasonic irradiation module device to an imaging position of the ultrasonic probe.

3. The apparatus of claim 1, wherein the processor is further configured to:
generate a notification based on an irradiation position of the ultrasonic irradiation device coinciding with an imaging position of the ultrasonic probe.

4. The apparatus of claim 3, wherein the processor is further configured to:
control the ultrasonic irradiation device to irradiate ultrasound based on the irradiation position of the ultrasonic irradiation device coinciding with the imaging position of the ultrasonic probe.

5. The apparatus of claim 4, wherein the processor is further configured to:
control the ultrasonic irradiation device to irradiate ultrasound with a respective intensity corresponding to a respective target distance based on the sensing distance being the respective target distance.

6. The apparatus of claim 1, wherein the processor is further configured to:
receive a tumor position of a tumor of the body obtained from the ultrasonic irradiation device; and
control the ultrasonic irradiation device to irradiate ultrasound with a respective intensity corresponding to a respective target position based on the tumor position being at the respective target position.

7. The apparatus of claim 1, wherein the processor is further configured to:
receive a tumor size of a tumor of the body obtained from the ultrasonic irradiation device, and
control the ultrasonic irradiation device to irradiate ultrasound with a respective intensity corresponding to a respective size based on the tumor size being the respective size.

8. A method for positioning an ultrasonic irradiation device, comprising:
determining, by an apparatus, a moving position based on a first offset value stored in a memory, a second offset value stored in a memory, and a distance value, wherein the first offset value corresponds to a distance between an ultrasonic probe and a marker, wherein the second offset value corresponds to a distance between the ultrasonic irradiation device and a camera, and wherein the distance value corresponds to a distance between a center position of the camera and a position of the marker in an image obtained from the camera; and
controlling, by the apparatus, the ultrasonic irradiation device and/or a bed to move based on the determined moving position to match the position of the marker with the center position of the camera; and
wherein the method further comprises: maintaining, by the apparatus, a predetermined distance between the ultrasonic irradiation device and the ultrasonic probe or a predetermined distance between the ultrasonic irradiation device and a body based on a sensing distance obtained from a distance sensor of the ultrasonic irradiation device.

9. The method according to claim 8, further comprising:
receiving an input of the first offset value and the second offset value through a correction user interface (UI);
storing the first offset value and the second offset value in the memory; and controlling a movement of the bed along an X-axis and a Y-axis to match an irradiation position of the ultrasonic irradiation device to an imaging position of the ultrasonic probe.

10. The method according to claim 8, further comprising: generating a notification based on an irradiation position of the ultrasonic irradiation device coinciding with an imaging position of the ultrasonic probe.

11. The method according to claim 10, further comprising:

controlling the ultrasonic irradiation device to irradiate ultrasound based on the irradiation position of the ultrasonic irradiation device coinciding with the imaging position of the ultrasonic probe.

12. The method according to claim 11, further comprising:

controlling the ultrasonic irradiation device to irradiate ultrasound with a respective intensity corresponding to a respective target distance based on the sensing distance being the respective target distance.

13. The method according to claim 8, further comprising: receiving a tumor position of a tumor of the body obtained from the ultrasonic irradiation device; and controlling the ultrasonic irradiation device to irradiate ultrasound with a respective intensity corresponding to a respective target position based on the tumor position being at the respective target position.

14. The method according to claim 8, further comprising: receiving a tumor size of a tumor of the body obtained from the ultrasonic irradiation device, and controlling the ultrasonic irradiation device to irradiate ultrasound with a respective intensity corresponding to a respective size based on the tumor size being the respective size.

15. A non-transitory computer-readable medium having processor-executable instructions stored thereon for positioning an ultrasonic irradiation device, wherein the processor-executable instructions, when executed, facilitate performance of the following:

determining, by an apparatus, a moving position based on a first offset value stored in a memory, a second offset value stored in a memory, and a distance value, wherein the first offset value corresponds to a distance between an ultrasonic probe and a marker, wherein the second offset value corresponds to a distance between the ultrasonic irradiation device and a camera, and wherein the distance value corresponds to a distance between a center position of the camera and a position of the marker in an image obtained from the camera; and controlling, by the apparatus, the ultrasonic irradiation device and/or a bed to move based on the determined moving position to match the position of the marker with the center position of the camera; and wherein the processor-executable instructions, when executed, further facilitate performance of the following: maintaining, by the apparatus, a predetermined distance between the ultrasonic irradiation device and the ultrasonic probe or a predetermined distance between the ultrasonic irradiation device and a body based on a sensing distance obtained from a distance sensor of the ultrasonic irradiation device.

16. The non-transitory computer-readable medium according to claim 15, wherein the processor-executable instructions, when executed, further facilitate performance of the following:

receiving an input of the first offset value and the second offset value through a correction user interface (UI);

storing the first offset value and the second offset value in the memory; and controlling a movement of the bed along an X-axis and a Y-axis to match an irradiation position of the ultrasonic irradiation device to an imaging position of the ultrasonic probe.

17. The non-transitory computer-readable medium according to claim 15, wherein the processor-executable instructions, when executed, further facilitate performance of the following:

generating a notification based on an irradiation position of the ultrasonic irradiation device coinciding with an imaging position of the ultrasonic probe.

18. The non-transitory computer-readable medium according to claim 17, wherein the processor-executable instructions, when executed, further facilitate performance of the following:

controlling the ultrasonic irradiation device to irradiate ultrasound based on the irradiation position of the ultrasonic irradiation device coinciding with the imaging position of the ultrasonic probe.

19. The non-transitory computer-readable medium according to claim 18, wherein the processor-executable instructions, when executed, further facilitate performance of the following:

controlling the ultrasonic irradiation device to irradiate ultrasound with a respective intensity corresponding to a respective target distance based on the sensing distance being the respective target distance.

20. The non-transitory computer-readable medium according to claim 15, wherein the processor-executable instructions, when executed, further facilitate performance of the following:

receiving a tumor position of a tumor of the body obtained from the ultrasonic irradiation device; and controlling the ultrasonic irradiation device to irradiate ultrasound with a respective intensity corresponding to a respective target position based on the tumor position being at the respective target position.

* * * * *